(12) United States Patent
Thramann et al.

(10) Patent No.: US 7,942,904 B2
(45) Date of Patent: May 17, 2011

(54) PEDICLE SCREW BASED VERTEBRAL BODY STABILIZATION APPARATUS

(75) Inventors: Jeff Thramann, Longmont, CO (US); Michael Fulton, Broomfield, CO (US)

(73) Assignee: Lanx, Inc., Broomfield, CO (US)

( * ) Notice: Subject to any disclaimer, the term of this patent is extended or adjusted under 35 U.S.C. 154(b) by 1279 days.

(21) Appl. No.: 11/383,326

(22) Filed: May 15, 2006

(65) Prior Publication Data

US 2007/0043360 A1 Feb. 22, 2007

Related U.S. Application Data

(63) Continuation-in-part of application No. 11/128,962, filed on May 12, 2005, now abandoned.

(51) Int. Cl.
*A61B 17/70* (2006.01)
(52) U.S. Cl. ...................................................... 606/257
(58) Field of Classification Search ................... 606/246, 606/248, 249, 254, 255, 257, 263, 264, 265, 606/270, 283, 299, 301, 302, 304, 76; 623/17.11–17.16, 23.41, 23.52, 23.57
See application file for complete search history.

(56) References Cited

U.S. PATENT DOCUMENTS

| | | |
|---|---|---|
| 4,599,085 A | 7/1986 | Riess et al. |
| 4,653,481 A | 3/1987 | Howland et al. |
| 5,005,562 A | 4/1991 | Cotrel |
| 5,074,864 A | 12/1991 | Cozad et al. |
| 5,147,359 A | 9/1992 | Cozad et al. |
| 5,154,718 A | 10/1992 | Cozad et al. |
| 5,180,393 A | 1/1993 | Commarmond |
| 5,201,734 A | 4/1993 | Cozad et al. |
| 5,306,275 A | 4/1994 | Bryan |
| 5,470,333 A | 11/1995 | Ray |
| 5,496,318 A | 3/1996 | Howland et al. |
| 5,531,745 A | 7/1996 | Ray |
| 5,609,634 A | 3/1997 | Voydeville |
| 5,645,599 A | 7/1997 | Samani |
| 5,658,335 A | 8/1997 | Allen |
| 5,683,390 A | 11/1997 | Metz-Stavenhagen et al. |
| 5,683,404 A | 11/1997 | Johnson |
| 5,725,582 A | 3/1998 | Bevan et al. |
| 5,800,550 A | 9/1998 | Sertich |
| 5,836,948 A | 11/1998 | Zuckerman et al. |
| 6,113,602 A | 9/2000 | Sand |
| 6,135,772 A | 10/2000 | Jones |
| 6,156,040 A | 12/2000 | Yonemura et al. |

(Continued)

FOREIGN PATENT DOCUMENTS

EP 0322334 A1 6/1989

(Continued)

OTHER PUBLICATIONS

International Searching Authority "Notification of Transmittal of the International Search Report and the Written Opinion of the International Searching Authority, or the Declaration" Apr. 29, 2008.

(Continued)

*Primary Examiner* — Eduardo C Robert
*Assistant Examiner* — David Comstock
(74) *Attorney, Agent, or Firm* — Holland & Hart LLP

(57) ABSTRACT

A pedicle screw stabilization device comprises a superior and inferior pedicle screw anchor with a shaped memory alloy spacer therebetween.

26 Claims, 4 Drawing Sheets

U.S. PATENT DOCUMENTS

| | | |
|---|---|---|
| 6,277,094 B1 | 8/2001 | Schendel |
| 6,293,949 B1 | 9/2001 | Justis et al. |
| 6,440,169 B1 | 8/2002 | Elberg et al. |
| 6,451,019 B1 | 9/2002 | Zucherman et al. |
| 6,548,569 B1 | 4/2003 | Williams et al. |
| 6,582,433 B2 | 6/2003 | Yun |
| 6,599,294 B2 | 7/2003 | Fuss et al. |
| 6,626,944 B1 | 9/2003 | Taylor |
| 6,635,060 B2 | 10/2003 | Hanson et al. |
| 6,641,582 B1 | 11/2003 | Hanson et al. |
| 6,652,527 B2 | 11/2003 | Zucherman et al. |
| 6,719,795 B1 | 4/2004 | Cornwall et al. |
| 6,761,720 B1 | 7/2004 | Senegas |
| 6,783,527 B2 | 8/2004 | Drewry et al. |
| 6,800,084 B2 | 10/2004 | Davison et al. |
| 6,824,565 B2 | 11/2004 | Muhanna et al. |
| 6,838,493 B2 | 1/2005 | Williams et al. |
| 7,018,379 B2 | 3/2006 | Drewry et al. |
| 7,029,475 B2 | 4/2006 | Panjabi |
| 2001/0012938 A1 | 8/2001 | Zuckerman et al. |
| 2002/0029039 A1 | 3/2002 | Zucherman et al. |
| 2002/0095154 A1* | 7/2002 | Atkinson et al. ............ 606/61 |
| 2002/0147449 A1 | 10/2002 | Yun |
| 2002/0156150 A1 | 10/2002 | Williams et al. |
| 2002/0173558 A1 | 11/2002 | Williams et al. |
| 2003/0153915 A1 | 8/2003 | Nekozuka et al. |
| 2003/0180266 A1 | 9/2003 | McKay et al. |
| 2003/0187509 A1 | 10/2003 | LeMole, Jr. |
| 2003/0216736 A1 | 11/2003 | Robinson et al. |
| 2003/0225021 A1 | 12/2003 | McKay et al. |
| 2004/0024458 A1 | 2/2004 | Senegas et al. |
| 2004/0059337 A1 | 3/2004 | Hanson et al. |
| 2004/0059339 A1 | 3/2004 | Roehm, III et al. |
| 2004/0106995 A1 | 6/2004 | Le Couedic et al. |
| 2004/0167520 A1 | 8/2004 | Zucherman et al. |
| 2004/0199168 A1 | 10/2004 | Bertagnoli et al. |
| 2005/0055096 A1* | 3/2005 | Serhan et al. ............ 623/17.11 |
| 2005/0085812 A1 | 4/2005 | Sherman et al. |
| 2005/0143737 A1 | 6/2005 | Pafford et al. |
| 2005/0240266 A1* | 10/2005 | Kuiper et al. ............ 623/17.11 |
| 2006/0271055 A1 | 11/2006 | Thramann |

FOREIGN PATENT DOCUMENTS

| | | |
|---|---|---|
| WO | WO 2004/073533 A1 | 8/2004 |

OTHER PUBLICATIONS

International Bureau Notification Concerning Transmittal of International Preliminary Report on Patentability (Chapter I of the Patent Cooperation Treaty) Nov. 27, 2008.

Search Report issued May 13, 2008 for Application No. PCT/US2007/081542.

* cited by examiner

PEDICLE SCREW BASED VERTEBRAL BODY STABILIZATION APPARATUS

RELATED APPLICATIONS

This application is a continuation in part under 35 U.S.C. §120 of U.S. patent application Ser. No. 11/128,962, titled Pedicle Screw Based Vertebral Body Stabilization Apparatus, filed May 12, 2005, incorporated herein as if set out in full.

FIELD OF THE INVENTION

The present invention relates to vertebral body stabilization and support and, more particularly, to a pedicle screw based system providing flex restrictions on vertebral bodies.

BACKGROUND OF THE INVENTION

Surgical techniques to correct or address spinal problems are turning more and more to non-fusion technologies. One type technology involves spinous process stabilization. Spinous process stabilization is further explained in U.S. patent application Ser. No. 11/128,960 filed, May 12, 2005, titled SPINAL STABILIZATION, which application is incorporated herein as if set out in full. Another similar technology comprises using conventional pedicle screws.

One conventional pedicle based stabilization system includes a pedicle screw platform threaded into at least a superior and inferior pedicle. Stabilizing cords a placed and spacers inserted between sets of pedicle screws. Once everything is placed, the cords are tightened.

Conventional pedicle based systems, such as the one explained above, provide adequate support, however, any flex of the system is abruptly stopped by either the cord or the spacer. Even if the spacer provides for some flex, the cord provides an abrupt stop in the opposite direction.

Some pedicle screw stabilization devices provide tracks to allow some movement. For example, the spacer may have elongated slots or tracks on the superior and/or inferior end the spacer to move relative to the pedicle screw, which allows for some relative movement between the superior and inferior vertebrae. The track provides more flex than the spacer/cord systems, but provides abrupt stops in both directions.

However, one problem with a pedicles screw based systems is over time the pedicle screws loosen and the stabilization device fails over time. The screws loosen, in part, because the motion inhibits the screw from fusing to the bone.

Thus, it would be desirous to develop a pedicle screw based spinal stabilization apparatus that provide a mechanism to prompt fusion.

SUMMARY OF THE INVENTION

To attain the advantages and in accordance with the purpose of the invention, as embodied and broadly described herein, a pedicle screw based spinal stabilization apparatus is provided. The apparatus uses materials specifically designed to dampen the movement to provide a gentle stop. The apparatus comprises a superior pedicle screw and an inferior pedicle screw. A spacer coupled to the superior pedicle screw and inferior pedicle screw allows compression and expansion of the vertebral bodies. At least a part of the spacer comprises elastic portion that dampens compression and expansion of the spacer to provide a relatively gentle stop to motion. Moreover, the elastic portion comprises a rigid degradable portion to make the elastic portion relatively inelastic until the degradable portion degrades.

The foregoing and other features, utilities and advantages of the invention will be apparent from the following more particular description of a preferred embodiment of the invention as illustrated in the accompanying drawings.

BRIEF DESCRIPTION OF THE DRAWING

The accompanying drawings, which are incorporated in and constitute a part of this specification, illustrate embodiments of the present invention, and together with the description, serve to explain the principles thereof. Like items in the drawings are referred to using the same numerical reference.

DETAILED DESCRIPTION

Figure 1:
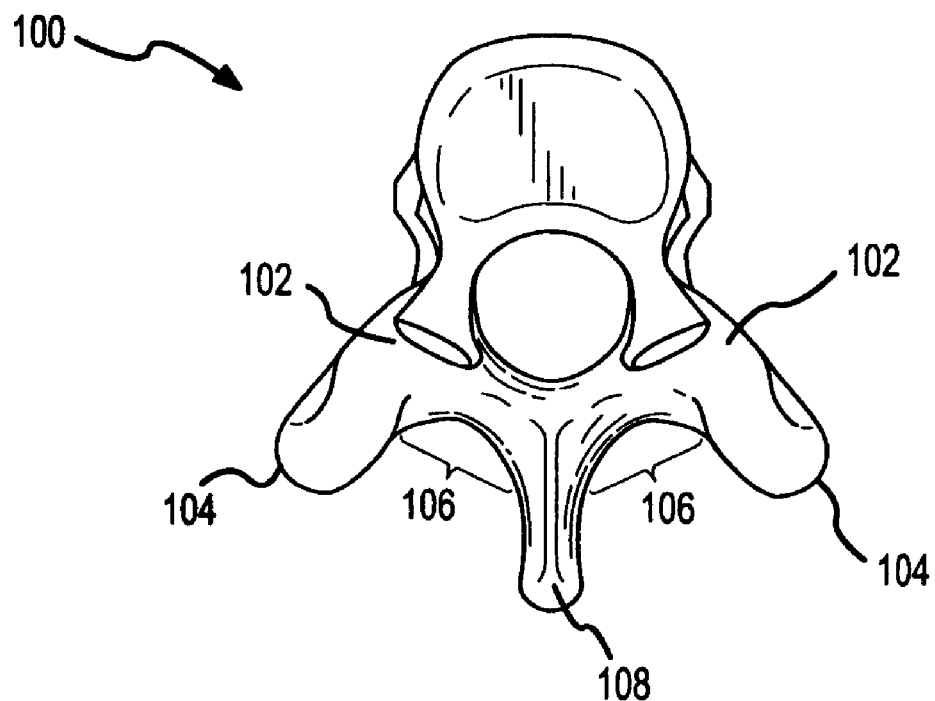
FIG. 1 shows a superior view of a vertebral body.
Figure 2:
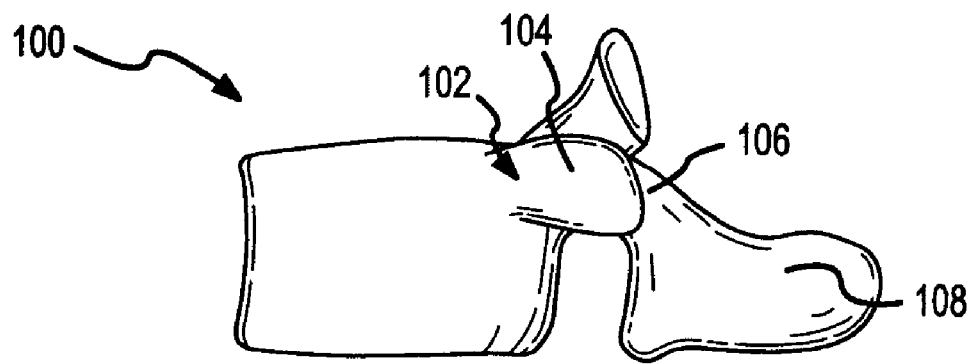
FIG. 2 shows an elevation view of the vertebral body of FIG. 1.

The present invention will now be described with reference to FIGS. 1 to 5. Referring first to FIGS. 1 and 2, a vertebral body 100 is shown for reference. FIG. 1 shows a superior view of a vertebral body 100 (i.e., looking down the spinal column). The vertebral body 100 comprises, among other parts, the pedicles 102, the facets 104, the lamina 106, and the spinous process 108. FIG. 2 shows a side elevation view of vertebral body 100 with a pedicle 102, the facet 104, lamina 106, and spinal process 106.

Figure 3:
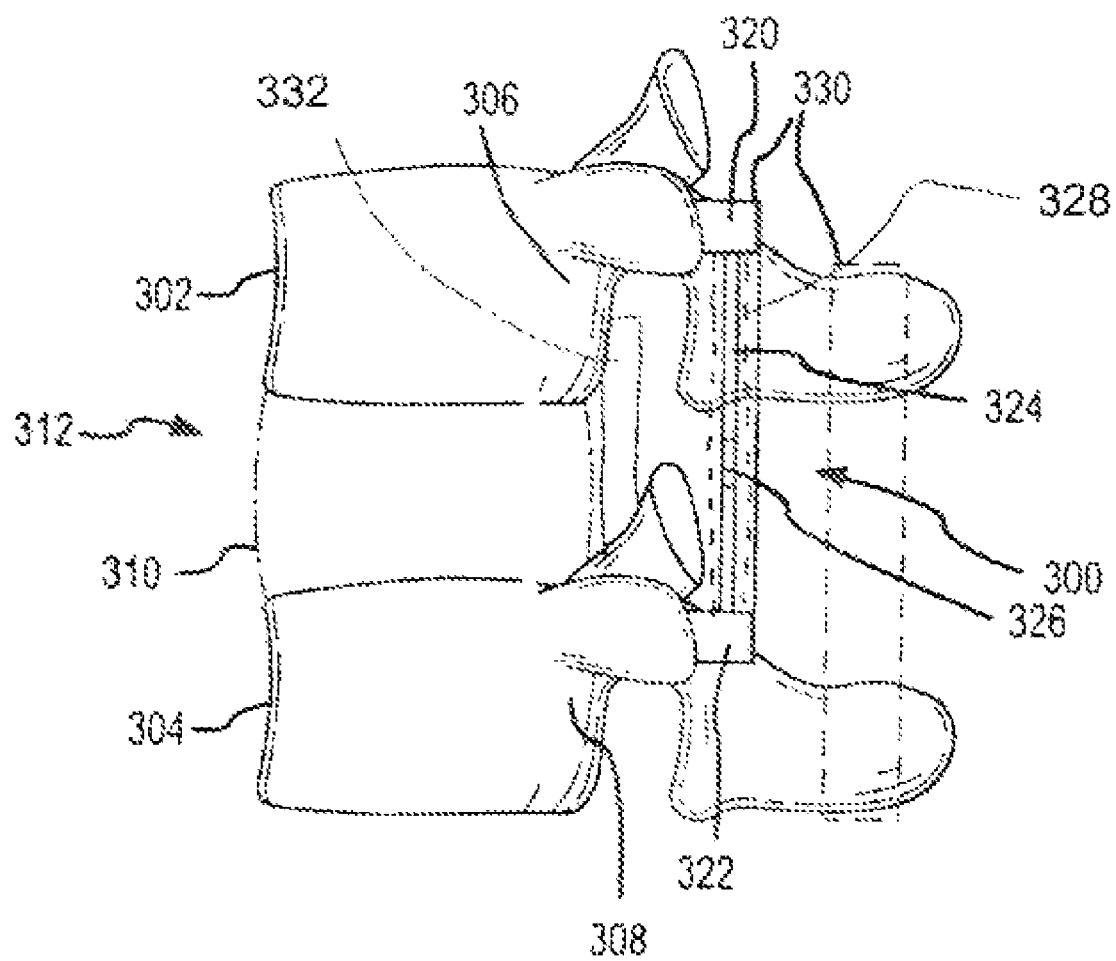
FIG. 3 shows a superior vertebral body and an inferior vertebral body with a pedicle screw based spacer consistent with an embodiment of the present invention.

FIG. 3 shows a side elevation view of a superior vertebral body 302 and an inferior vertebral body 304 (not shown to scale and slightly exploded for ease of reference) with a pedicle screw stabilization device 300. For reference, vertebral bodies 302 and 304 comprise the superior pedicle 306 and the inferior pedicle 308. An intervertebral disk 310 typically exists in intervertebral space 312, but may be removed and/or replace by artificial discs, grafts, or the like.

Device 300 comprises a superior pedicle screw 320 and an inferior pedicle screw 322. A spacer 324 is coupled to the pedicle screws. Spacer 324 includes a elastic/damper portion 326 that allows some expansion and contraction between the vertebral bodies. While shown as a single piece, spacer 324 could be multiple pieces. When multiple pieces are provided, parts may provide dampening in one or both directions as desired. Portion 326 is shown centrally located on spacer 324, but could be located elsewhere and/or be the entire spacer 324. In either direction, the resistance to the motion would increase to provide a relatively gentle stop to the motion instead of the abrupt stop associated with conventional stabilization devices. Spacer 324 could be made our of polymers or other biocompatible material, but it is preferred to construct spacer 324 from shaped memory alloys because of their elastic qualities at conventional body temperatures. Spacer 324 could be attached to pedicle screws 320 and 322 in any conventional manner. Moreover, while show as a single level stabilization, device 300 could be used for multiple level stabilization.

Optionally, a band 330 can be used to further inhibit flex of the spine. Band 330 can be wrapped about superior pedicle screw 320 and inferior pedicle screw 322. Alternatively, band 330 can be wrapped about other parts of the vertebral body. For example, band 330 could be wrapped about the spinous process of superior vertebral body 302 and the spinous process of the inferior vertebral body 304 as shown in phantom. Band 330 could be any conventional biocompatible material, such as, for example, metals, shaped memory alloys, polymers, PEEK, or the like. Band 330 could be a circular, elliptical, or other shape band or attach similar to a "C" clamp or the like such that band 330 only has a single side.

As mentioned, one problem with pedicle based system is the tendency of the pedicles screws to loosen over time. The loosening in part is due to the motion between the vertebral bodies inhibiting the pedicle screw from fusing the pedicle. To facilitate fusing, a sheath 328 of degradable material may be formed around spacer 324. Sheath 328 should be relatively inflexible and cause the vertebral segment to move in unison. Sheath may comprise resorbable material, for example. Alternatively, sheath 328 could be a non-degradable but removable material that could be surgically removed after a predetermined length of time. Sheath 328, while shown over the entire spacer 324 may be limited to an area proximate the elastic portion 326 of spacer 324. Moreover, instead of a sheath 328, band 330 may comprise the degradable material to inhibit relative motion and prompt fusion. Still alternatively, instead of sheath 328, a spinal plate 332 comprising degradable material may be used to inhibit initial movement. Once the relatively inelastic degradable portion degrades or absorbs, the device would function as described. Sheath 328 may be internal to spacer 324 as well. If internal to spacer 324, spacer 324 may have perforations to facilitate degrading or absorbing of the material. If spacer 324 or elastic portion 326 comprise shaped memory alloy, sheath 328 could be replaced by providing shaped memory alloy spacer in its relatively inelastic state and after a sufficient amount of time, activating the shaped memory alloy such that it enters its elastic phase.

Figure 4:
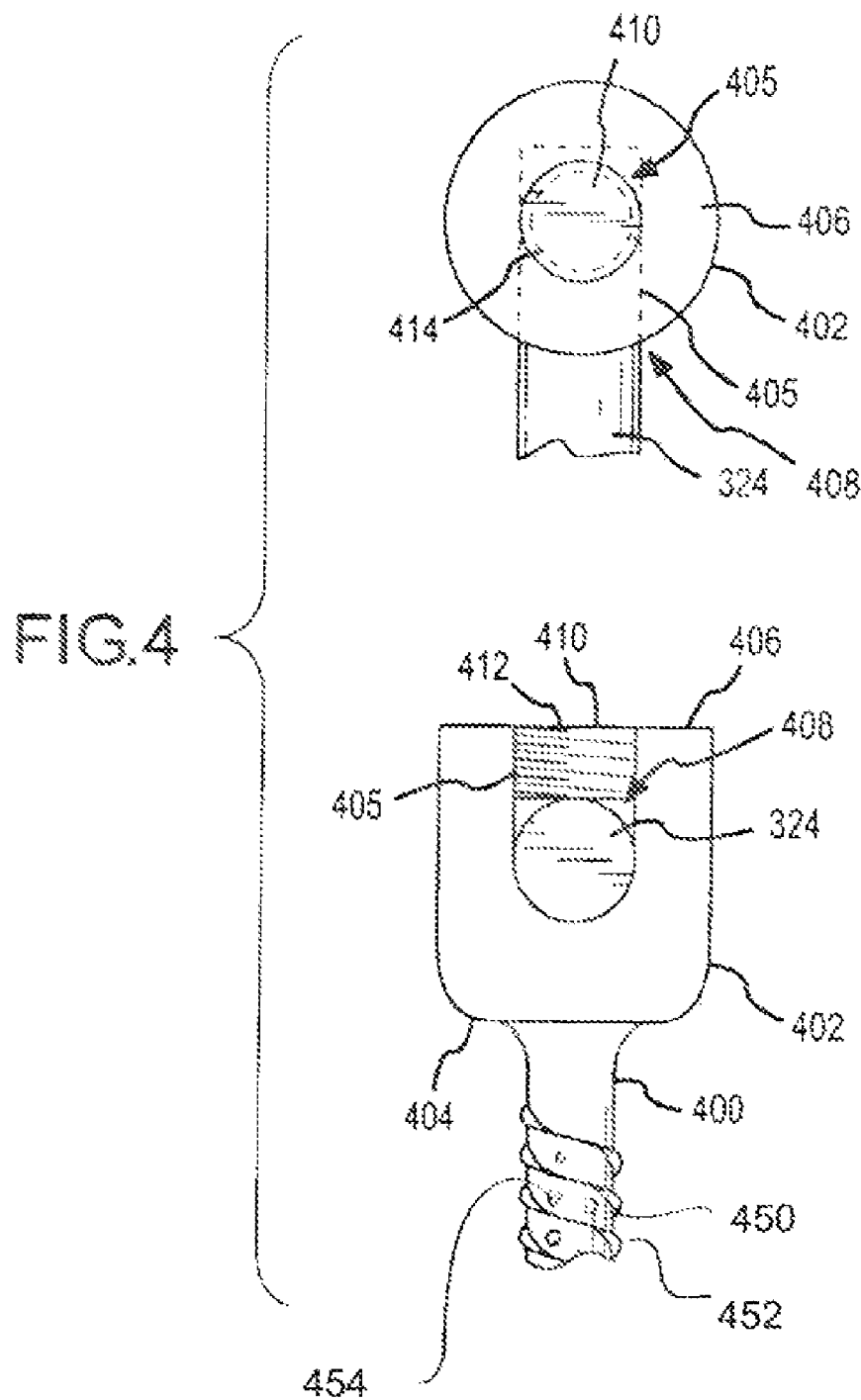
FIG. 4 shows a pedicle screw and anchor consistent with an embodiment of the present invention.

FIG. 4 shows a top and side view of pedicle screw 400 and anchor 402 to which a spacer 324 may be attached. Anchor 402 has a bone engaging surface 404 and a top 406 opposite the bone engaging 404. A bore 405 extends from the top 406 to the bone engaging surface 404. A channel 408 extends from the top 406 towards bone engaging surface 404. Channel 408 is designed to fit spacer 324. Channel 408 may be open on two sides of anchor 402, similar to a spinal rod system, or open on a single side of anchor 402 (as shown). A setscrew 410 having first threads 412 it threaded onto corresponding threads 414 in bore 405 to couple spacer 324 to pedicle screw 400 and anchor 402. To facilitate the pedicle screws being permanently threaded into pedicles, thread 450 may be coated with bone growth materials 452, as those materials are conventionally understood in the art. Moreover, the pedicle screws may include bone growth channels 454 to promote bone growth through the pedicle screws. Channels 454 may be coated and/or packed with bone growth material. As one of skill in the art would now recognize, the pedicle screws may be similar to bone growth cages. The bone growth devices along with sheath 328 should prompt fusing the pedicle screw to the bone.

Figure 5:
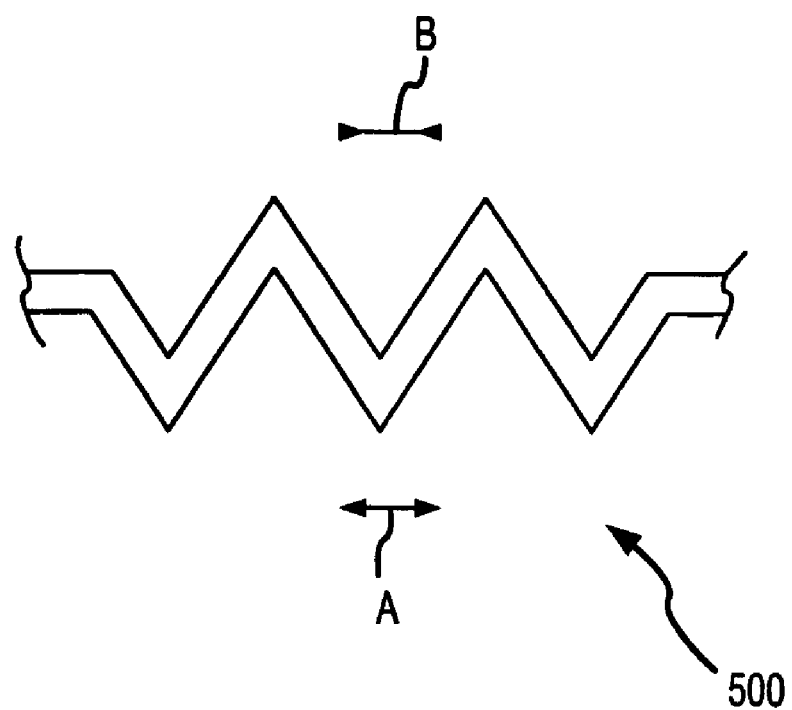
FIG. 5 shows a possible shape of a portion of the spacer of FIG. 3.

As mentioned above, spacer 324 and/or portion 326 could be constructed out of a number of materials to provide elastic movement in multiple directions. FIG. 5 shows an optional and possible construction of spacer 324 and/or portion 326 to facilitate expansion and compression of spacer 324. FIG. 5 shows an accordion shape section 500. Section 500 can expand in direction A on application of tension. Section 500 can compress in direction B on application of compression. Using an accordion shape, as section 500 becomes more elongated and/or more compact, the force resisting movement increases to provide a dampening effect. The dampening effect provides a more gentle stop than conventional pedicle screw based stabilization devices.

While the invention has been particularly shown and described with reference to an embodiment thereof, it will be understood by those skilled in the art that various other changes in the form and details may be made without departing from the spirit and scope of the invention.

We claim:

1. A screw based spinal stabilization device, comprising:
   a superior screw;
   an inferior screw;
   a spacer coupled to the superior screw and inferior screw, the spacer allows compression and expansion of vertebral bodies and comprises an elastic portion to allow relative movement between the superior screw and the inferior screw that dampens compression and expansion of the spacer to provide a relatively gentle stop to motion; and
   a sheath of substantially inelastic material comprising a degradable material abutting the spacer to inhibit relative motion between the superior screw and the inferior screw for a period of time, a first configuration of the sheath of substantially inelastic material, during the period of time and prior to degradation, inhibiting relative motion between the screws so as to promote fusion of the superior screw and the inferior screw to the vertebral bodies, and a second configuration of the sheath of substantially inelastic material, after the period of time and degradation, allowing relative motion between the screws.

2. The device of claim 1, wherein the spacer is constructed from shaped memory alloy.

3. The device of claim 2, wherein the shaped memory alloy is nickel-titanium.

4. The device of claim 1, wherein the sheath is external to the spacer.

5. The device of claim 1, wherein the degradable material is resorbable material.

6. The device of claim 1, wherein the superior screw and the inferior screw each comprise an anchor, wherein the anchor includes a bone engaging surface and a top opposite the bone engaging surface, a channel resides in the anchor extending from the top towards the bone engaging surface, the channel being sized to fit the spacer, and a setscrew is threaded into the channel to lock the spacer in the channel.

7. The device of claim 1, wherein the sheath extends over the entire spacer.

8. The device of claim 1, wherein at least one of the superior screw and the inferior screw carries bone growth material.

9. The device of claim 1, wherein at least one of the superior screw and the inferior screw comprises at least one bone growth channel.

10. The device of claim 1, wherein the sheath of substantially inelastic material is proximate the elastic portion of the spacer.

11. The device of claim 10, wherein the sheath of substantially inelastic material is limited to an area proximate the elastic portion of the spacer.

12. The device of claim 1, wherein the sheath of substantially inelastic material is formed partially around the spacer.

13. The device of claim 1, wherein the sheath of substantially inelastic material is formed completely around the spacer.

14. The device of claim 1, wherein the sheath of substantially inelastic material is formed aligned with, and at least partially around, the spacer.

15. The device of claim 1, wherein the sheath of substantially inelastic material is disposed internal to the spacer.

16. The device of claim 1, wherein the spacer further comprises a plurality of perforation adapted to facilitate degrading of the sheath.

17. The device of claim 1, wherein the second configuration of the sheath occurs after partial degradation of the sheath.

18. A screw based spinal stabilization device, comprising:
a superior screw;
an inferior screw;
a spacer coupled to the superior screw and inferior screw, the space allows compression and expansion of the vertebral bodies and comprises an elastic portion to allow relative movement between the superior screw and the inferior screw that dampens compression and expansion of the spacer to provide a relatively gentle stop to motion; and
a band of substantially inelastic material comprising a degradable material, the band coupled to the superior screw and the inferior screw to inhibit relative motion between the superior screw and the inferior screw for a period of time, a first configuration of the band of substantially inelastic material, during the period of time and prior to degradation, inhibiting relative motion between the screws so as to promote fusion of the superior screw and the inferior screw to the vertebral bodies, and a second configuration of the band of substantially inelastic material, after the period of time, allowing relative motion between the screws.

19. The device of claim 18, wherein the band is coupled to the superior spinous process and the inferior spinous process.

20. The device of claim 18, wherein the band comprises a plate coupled to at least the superior vertebral body and the inferior vertebral body.

21. The device of claim 18, wherein the degradable material is resorbable material.

22. The device of claim 18, wherein at least one of the superior screw and the inferior screw carries bone growth material.

23. The device of claim 18, wherein at least one of the superior screw and the inferior screw comprises at least one bone growth channel.

24. A screw based spinal stabilization device, comprising:
a superior screw;
an inferior screw; and
a spacer coupled to the superior screw and inferior screw, a degradable material abutting the spacer to inhibit relative motion between the superior screw and the inferior screw for a period of time, the spacer having a substantially inelastic state for a period of time and a substantially elastic state after the period of time, whereby in the inelastic state the spacer inhibits relative movement between the superior screw and the inferior screw to promote fusion of the superior screw and the inferior screw to the superior body and inferior body, respectively, and whereby in the elastic state the spacer allows compression and expansion of the vertebral bodies and comprises an elastic portion to allow relative movement between the superior pedicle screw and the inferior pedicle screw that dampens compression and expansion of the spacer to provide a relatively gentle stop to motion.

25. The device of claim 24, wherein the spacer comprises at least one shaped memory alloy.

26. A screw based spinal stabilization device, comprising:
a superior screw;
an inferior screw;
a spacer coupled to the superior screw and inferior screw, the spacer allows compression and expansion of vertebral bodies and comprises an elastic portion to allow relative movement between the superior screw and the inferior screw that dampens compression and expansion of the spacer to provide a relatively gentle stop to motion; and
a sheath of substantially inelastic material comprising a degradable material abutting the spacer to inhibit relative motion between the superior screw and the inferior screw for a period of time;
wherein the combined spacer and sheath have a first configuration during the period of time and prior to degradation of the sheath, the sheath inhibiting relative motion between the screws so as to promote fusion of the superior screw and the inferior screw to the vertebral bodies;
wherein the combined spacer and sheath have a second configuration after the period of time and degradation of the sheath, allowing relative motion between the screws.

* * * * *